US011291418B2

(12) United States Patent
He (10) Patent No.: US 11,291,418 B2
(45) Date of Patent: Apr. 5, 2022

(54) BACKSCATTERING X-RAY IMAGER WITH X-RAY SOURCE AT DETECTOR CENTER

(71) Applicant: HOLOGIC, INC., Marlborough, MA (US)

(72) Inventor: Shusheng He, Newark, DE (US)

(73) Assignee: Hologic, Inc., Marlborough, MA (US)

( * ) Notice: Subject to any disclaimer, the term of this patent is extended or adjusted under 35 U.S.C. 154(b) by 235 days.

(21) Appl. No.: 16/413,918

(22) Filed: May 16, 2019

(65) Prior Publication Data

US 2019/0350546 A1 Nov. 21, 2019

Related U.S. Application Data

(60) Provisional application No. 62/672,243, filed on May 16, 2018.

(51) Int. Cl.
*A61B 6/00* (2006.01)
*A61B 6/06* (2006.01)

(52) U.S. Cl.
CPC .................. *A61B 6/42* (2013.01); *A61B 6/06* (2013.01); *A61B 6/4435* (2013.01); *A61B 6/4476* (2013.01); *A61B 6/483* (2013.01); *A61B 6/4071* (2013.01); *A61B 6/4078* (2013.01); *A61B 6/4458* (2013.01); *A61B 6/502* (2013.01)

(58) Field of Classification Search
CPC ....... A61B 6/06; A61B 6/4071; A61B 6/4078; A61B 6/4435; A61B 6/4476; A61B 6/483; A61B 6/502; A61B 6/4429; A61B 6/4458; A61B 6/42
See application file for complete search history.

(56) References Cited

U.S. PATENT DOCUMENTS

| 4,819,256 A * | 4/1989 | Annis .................... G01N 23/18 378/87 |
| 6,172,369 B1 * | 1/2001 | Waechter .......... H01L 27/14643 250/370.09 |
| 7,620,150 B1 * | 11/2009 | Annis .................... A61B 6/483 378/87 |
| 2008/0043913 A1 * | 2/2008 | Annis .................. G01V 5/0025 378/87 |
| 2011/0103554 A1 * | 5/2011 | Charette ............. G01V 5/0041 378/138 |
| 2013/0315369 A1 * | 11/2013 | Turner ............. G01N 23/20008 378/41 |
| 2017/0358380 A1 * | 12/2017 | Rothschild ........... G01V 5/0025 |
| 2019/0212466 A1 * | 7/2019 | Smith .................. A61B 6/4452 |
| 2020/0033274 A1 * | 1/2020 | Couture .............. G01N 23/203 |

* cited by examiner

*Primary Examiner* — Chih-Cheng Kao
(74) *Attorney, Agent, or Firm* — Merchant & Gould P.C.

(57) ABSTRACT

An apparatus including an x-ray source and detector where the source is disposed behind the detector and the detector is configured with a hole through which an x-ray beam emitted by the source can be transmitted to target tissue is provided. During operation, the source emits an x-ray beam through the hole in the detector. The x-ray beam may then be incident on an area of a subject to be imaged and cause various reflections and/or absorptions. The detector can detect signals reflected by the subject and an x-ray image can be generated accordingly.

24 Claims, 9 Drawing Sheets

BACKSCATTERING X-RAY IMAGER WITH X-RAY SOURCE AT DETECTOR CENTER

CROSS-REFERENCE TO RELATED APPLICATION

This application claims priority to U.S. Provisional Patent Application Ser. No. 62/672,243, filed on May 16, 2018, entitled "BACKSCATTERING X-RAY IMAGER WITH X-RAY SOURCE AT DETECTOR CENTER," the contents of which are incorporated herein by reference in their entirety.

FIELD OF THE DISCLOSURE

The disclosure relates generally to the field of x-ray imaging, and particularly to obtaining breast images of a patient.

BACKGROUND

Generally speaking, an x-ray source and detector are separated at opposing sides of a subject to be imaged. For example, for x-ray imaging of human breast tissue, the x-ray source and detector are separated at opposing sides of the tissue. Conventional x-ray techniques have some limitations, particularly in the field of mammography in which large gantries are utilized. For example, tissue located in areas where it is challenging to place the x-ray source and detector on opposing sides of the patient (e.g., tissue adjacent to the armpit, tissue on the upper part of the breast, tissue adjacent to the ribs, etc.) using conventional mammography techniques. Requiring the x-ray source and detector to be placed on opposing sides of tissue presents issues with, inter alia, proper patient positioning, patient comfort, and exposure technique for difficult to access tissue areas.

Some practitioners may use ultrasonic images to "fill in the gaps" where conventional x-ray imaging cannot be used. However, the sensitivity and resolution of ultrasound images lags behind that of x-ray images. Furthermore, due to the volume of x-ray images used for routine breast cancer screening, there is a large base of knowledge pertaining to reading x-ray images versus reading ultrasound images.

BRIEF DESCRIPTION OF THE DRAWINGS

By way of example, specific embodiments of the disclosed device will now be described, with reference to the accompanying drawings, in which.

DETAILED DESCRIPTION

Various examples, implementations, and illustrative configurations are described herein. It is to be appreciated that the various depictions are not drawn to scale; instead, they are drawn in a manner to facilitate understanding. Additionally, the various examples and illustrations can be combined with each other, even where not specifically so stated. Additionally, the described examples are not intended to limit the claims; instead, the present disclosure is presented such that the claimed subject matter will be thoroughly illuminated.

The present disclosure provides various apparatus and methods to capture an x-ray image where the x-ray source and detector are on the same side of the subject to be imaged. For example, the present disclosure provides an x-ray source and detector where the source is disposed behind the detector and the detector is configured with a hole through which an x-ray beam emitted by the source can be transmitted. During operation, the source emits an x-ray beam through the hole in the detector. The x-ray beam may then be incident on an area of a subject to be imaged, and cause various reflections and/or absorptions. The detector can detect signals reflected by the subject and an x-ray image can be generated accordingly.

In some examples, the present disclosure can be implemented to image human breast tissue. Such images might then be used to diagnose and treat potential breast cancers. It is to be appreciated, that in response to energetic x-rays, human breast tissue not only generates x-ray absorption but also Compton scattering, often referred to as Compton backscattering. Conventional applications for generating images from x-rays based on backscattering cannot be applied to human breast tissue. For example, the areas to be imaged respective to human breast tissue are significantly smaller than areas imaged using conventional backscattering techniques. As another example, anatomical structures such as the rib cage, individual ribs, heart, lungs, etc. may interfere and/or obstruct x-ray absorption and scattering when conventional backscattering techniques are applied to human breast tissue. Furthermore, conventional backscattering systems provide a pencil beam x-ray source disposed central to two detectors, which are disposed on opposite sides of the source. There are gaps between these two detectors and the source where reflected signals from the human breast tissue would be lost. As a result, x-ray images generated from these devices would not accurately reflect the state of the imaged tissue.

Accordingly, the present disclosure provides an x-ray imaging system that can be used to soft tissue, such as breast tissue and/or breast structure. In particular, the x-ray imaging system provided can be used to image human tissue where it is not feasible to place an x-ray source and detector on opposing sides of the tissue. In some examples, the provided x-ray imaging system can be used to capture images that are to augment, or supplement, images captured using conventional x-ray techniques. For example, images of a patient's breast tissue can be captured using conventional techniques while further images of the patient's breast tissue not captured by conventional techniques (e.g., adjacent to the armpit, in the upper chest area, etc.) can be captured using the systems and methods of the present disclosure. Thus, a complete set of mammographic images of the patient's breast tissue may be captured. In some applications, devices and techniques described herein can be used for routine breast cancer screening. With some applications, devices and techniques described herein can be used for diagnostic work-ups and/or interventional procedures including breast tissue biopsy.

Figure 1:
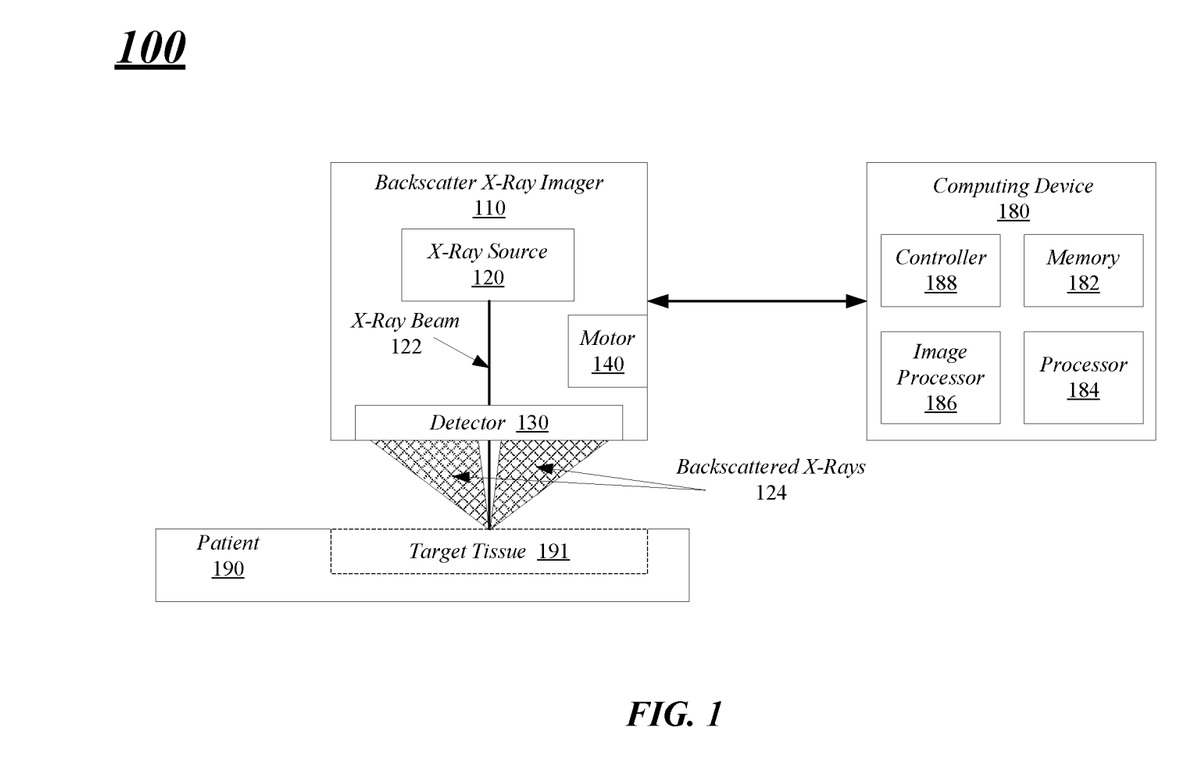
FIGS. 1-2 illustrate a first example x-ray imaging system according to some embodiments.
Figure 2:
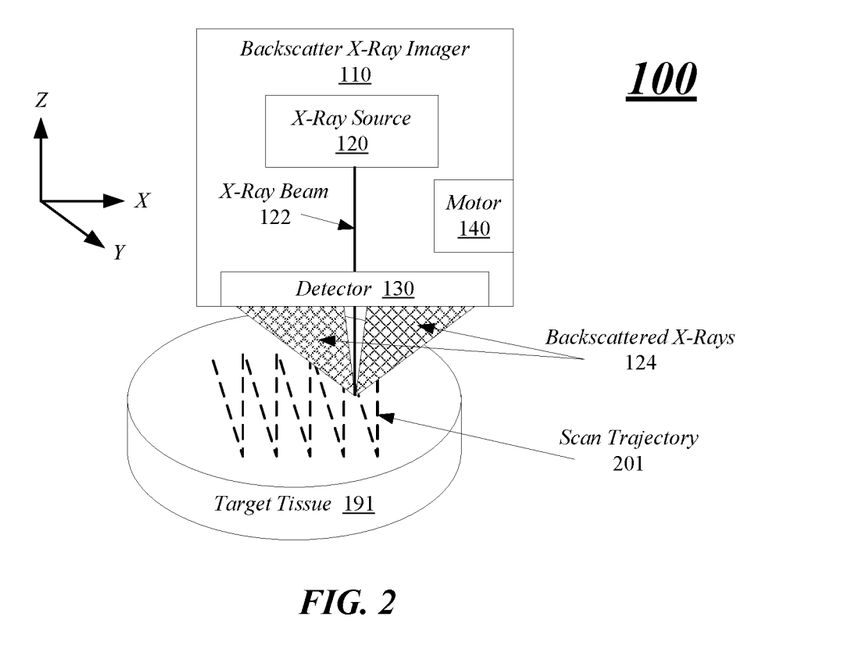

FIGS. 1-2 illustrate an example x-ray imaging system 100, which may be implemented according to various examples of the present disclosure. In general, the x-ray imaging system 100 provides a backscatter x-ray imager 110 and a computing device 180 arranged to generate images of a portion of a patient 190. Specifically, the system 100 is arranged to generate x-ray images of target tissue 191 of patient 190. In some examples, target tissue 191 can be breast tissue and/or tissue adjacent to a breast of patient 190. As a few specific examples, target tissue 191 may be tissue in an armpit of patient 190, tissue proximate the ribcage of patient 190, or tissue proximate the breast of patient 190 (e.g., upper chest area, area between the breast and collarbone, or the like).

System 100 could be implemented as part of a mammography and/or tomosynthesis system. For example, system 100 could be implemented to capture images of areas in which a conventional mammography and/or tomosynthesis system cannot properly image. Thus, a complete set of images for mammography and/or tomosynthesis may be obtained, and subsequently used by a health professional. With some implementations, the system 100 can be an accessory that is removably attached to a mammography and/or tomosynthesis system. For example, system 100 could be implemented as part of an additional imaging mode in a multi-modal imaging system.

Backscatter x-ray imager 110 includes an x-ray source 120 and a detector 130. In general, the x-ray source 120 is arranged to emit a pencil beam 122. Detector 130 is arranged with a hole (e.g. see FIGS. 4-6) to transmit pencil beam 122 to target tissue 191. The target tissue 191 causes scattering and absorption in the x-rays of pencil beam 122. Backscattered x-rays 124 are reflected by target tissue 191 towards backscatter x-ray imager 110. Detector 130 is arranged to detect the backscattered x-rays 124.

Computing device 180 is communicatively coupled to backscatter x-ray imager 110 and arranged to both provide control signals to backscatter x-ray imager 110 and receive information elements from backscatter x-ray imager 110. In some examples computing device 180 and backscatter x-ray imager 110 can each include communication interfaces (not shown) to facilitate coupling computing device 180 to backscatter x-ray imager 110 for purposes of exchanging data (e.g., information elements including indications of x-ray signals, control signals, or the like). Computing device 180 and backscatter x-ray imager 110 can be communicatively coupled via the communication interface in a wireless or wired communication scheme. Said differently, the above-mentioned communication interfaces could couple together via a wireless communication medium or channel or via a wired communication medium or channel. Examples are not limited in this context.

Computing device 180 can include a memory 182 and processor 184. Memory 182 may store information elements received from backscatter x-ray imager 110 including indications of backscattered x-rays 124 detected by detector 130. Memory 182 may also store instructions, such as, instructions executable by processor 184 that may cause processor 184 to perform actions dictated by the instructions. Computing device 180 may also include image processor 186 and controller 188. In some examples, image processor 186 and/or controller 188 may be implemented as instructions stored in memory 182. With some examples, image processor 186 and/or controller 188 may be implemented as circuitry or hardware components. In other examples, image processor 186 and/or controller 188 can be implemented as a combination of instructions stored in memory 182 and circuitry or hardware components.

Image processor 186 can form x-ray images of target tissue 191 from information elements received from backscatter x-ray imager 110. More specifically, image processor 186 may form x-ray images of target tissue 191 from indications of backscattered x-rays 124 detected by detector 130. Computing device 180 may include a display (not shown) to display images generated by image processor 186.

Controller 188 can be arranged to send control signals to backscatter x-ray imager 110 including indications of movements for x-ray source 120 and detector 130. Backscatter x-ray imager 110 can include a motor 140 coupled to x-ray source 120 and detector 130 and arranged to move x-ray source 120 and detector 130 in the x and y plane relative to the target tissue. For example, during operation, Controller 188 may send control signals to backscatter x-ray imager 110 including indication that cause motor 140 to move x-ray source 120 and detector 130 along a scan trajectory 201.

In some embodiments, computing device 180 could be a general purpose computer arranged to couple to backscatter x-ray imager 110 (e.g., via wired or wireless communication interfaces, or the like). For example, a manufacturer or supplier of backscatter x-ray imager could provide instructions (e.g., application software, device drivers, or the like) to be stored on memory 182 of computing device 180 while computing device 180 may be supplied by a user of system 100. In other embodiments, computing device 180 may be a logic device specifically designed, developed, configured, arranged, and/or the like to perform operations according to some embodiments. Embodiments are not limited in this context.

In some embodiments, at least a portion of computing device 180 can be included in or incorporated into backscatter x-ray imager 110. For example, at least memory 182 and processor 184 could be included in backscatter x-ray imager 110. As a further example, controller 188 could be included in backscatter x-ray imager 110. In such examples, backscatter x-ray imager 110 could send information elements (e.g., via a communication interface) including indications of signals from detector 130 to another computing device arranged to receive the information element and generate and/or display x-ray images as described herein.

In some embodiments, backscatter x-ray imager 110 includes motor 140 coupled to at least x-ray source 120 and detector 130. It is important to note that in some examples, motor 140 moves x-ray source 120 and detector 130 in tandem, such that, coordinates (e.g., x and y coordinates, or the like) where pencil beam 122 is incident on target tissue 191 and corresponding backscattered x-rays 124 are detected by detector 130 can be captured. With some examples, backscatter x-ray imager 110 could include multiple motors, for example a first motor coupled to x-ray source 120 and a second motor, different from the first motor, coupled to detector 130. These motors could be arranged to move the x-ray source 120 and detector 130 along the scan trajectory 201.

Image processor 186 can use these coordinates and the corresponding indications of backscattered x-rays 124 to form x-ray images of target tissue. With some examples, the indications of the backscattered x-rays 124 at each coordinate can be summed, integrated, or otherwise compiled to form x-ray images of target tissue 191. For example, image processor 186 can sum the indications of backscattered x-rays 124 at each coordinate and then form an x-ray image of the target tissue 191 from the summed backscattered x-rays 124.

Figure 3:
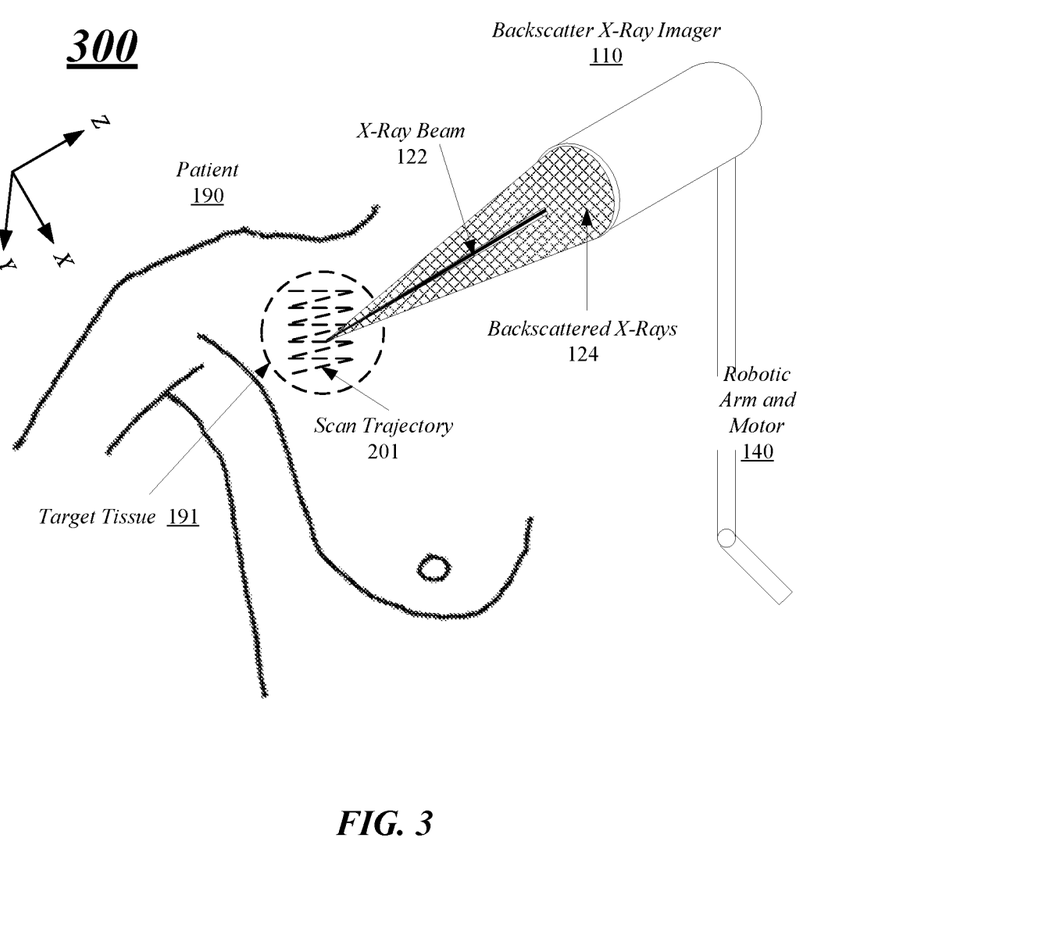
FIG. 3 illustrates a second example x-ray imaging system according to some embodiments.

FIG. 3 illustrates an example x-ray imaging system 300 as may be implemented to capture mammographic images of tissue proximate to a patient's breast. The system 300 may include many of the features and components depicted and described with respect to x-ray imaging system 100 of FIGS. 1-2. Target tissue 191 is depicted as an upper region above the breast of patient 191. During practice, patient 191 may be immobilized during the scanning and capturing of the x-ray images. For example, patient may be provided a chair in which to relax, forms may be provided to position patient in a desired location. As an alternative, patient may be positioned on a table in either a supine or a prone position. Where the patient is prone, the table may include an aperture to allow the breast to be pendant. Additionally, it is to be appreciated that standard safety protocols should be employed to shield the patient 190 from unwanted exposure to x-rays 122. The backscatter x-ray images 110 may be provided along with a robotic arm and motor system 140 arranged to move backscatter x-ray imager 110 along scan trajectory 201.

It is to be appreciated, that capturing an image of target tissue 191 using x-ray imaging system 300 (or 100 of FIGS. 1-2) may be slower than conventional x-ray imaging techniques. For example, backscatter x-ray imager 120 must be moved along the scan trajectory 201 to capture an image of target tissue. Accordingly, during practice an area over which scan trajectory 201 covers (e.g., a surface area of target tissue) may be limited based on the time available to capture the image. With some examples, the surface area of target tissue 191 can be between 6 and 15 centimeters squared ($cm^2$).

Figure 10:
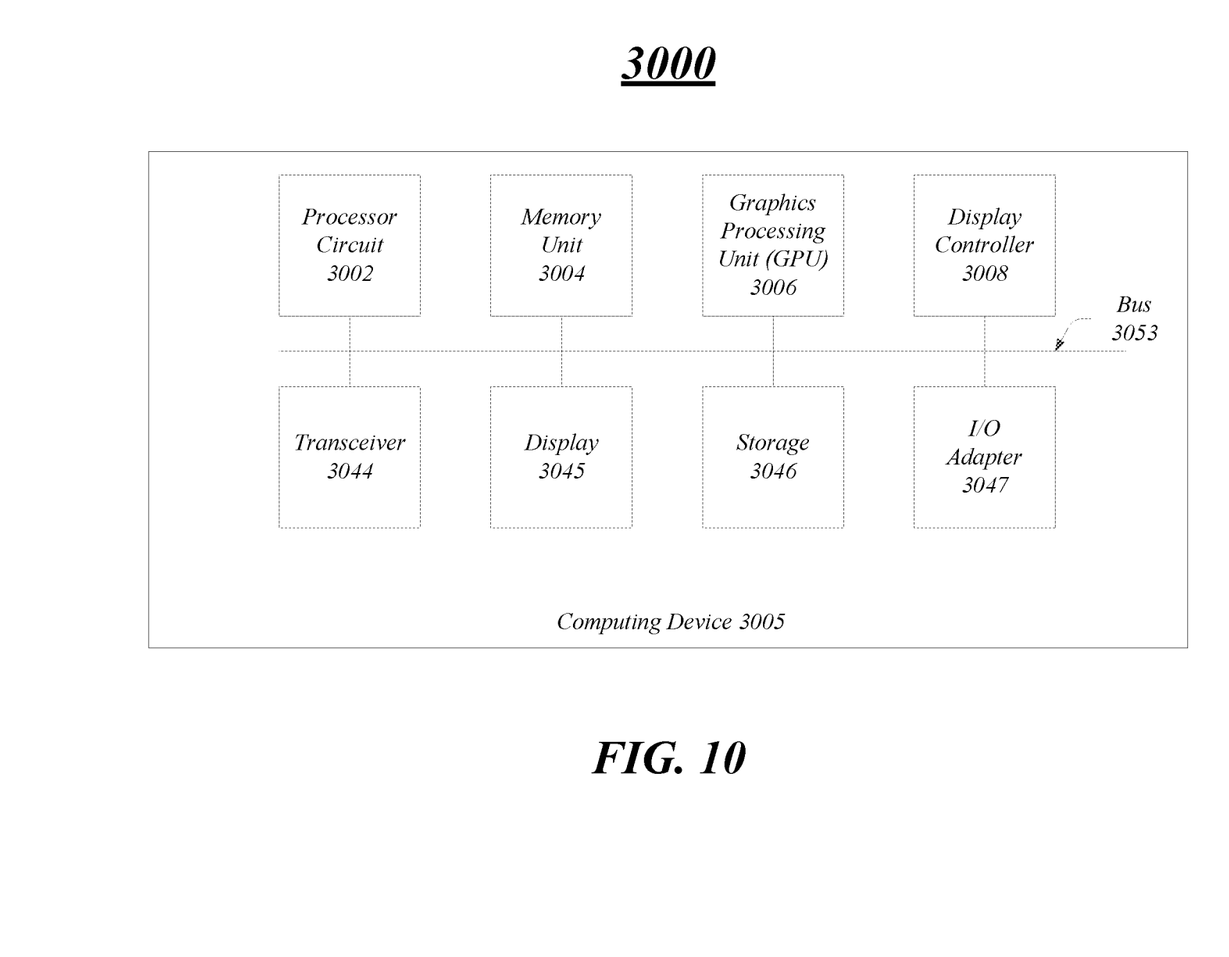
FIG. 10 illustrates a computing system according to some embodiments.

With some embodiments, the backscatter x-ray imager 110 from system 100 and/or system 300 could be coupled to a computing device (e.g., computing device 180, or the like) including a display (e.g., display 3045 of FIG. 10, or the like). The computing device can cause a user interface (e.g., graphics user interface, or the like) to be presented on the display. The user interface can provide information regarding scanning target tissue 191 of patient 190. For example, the user interface can provide indications of which portions of scan trajectory 201 have been scanned and/or have yet to be scanned. In some examples, the user interface can provide an image (e.g., picture, cartoon, or the like) of breast tissue and associated target tissue 191 depicting the area to be scanned along with indications of the scan trajectory 201 and/or scanning progress along the scan trajectory 201. The image of the target tissue 191 provided on the user interface can be generated, for example, from an optical imaging device (e.g., a camera, a stereoscopic camera, a structured light imaging device, or the like).

Figure 4:
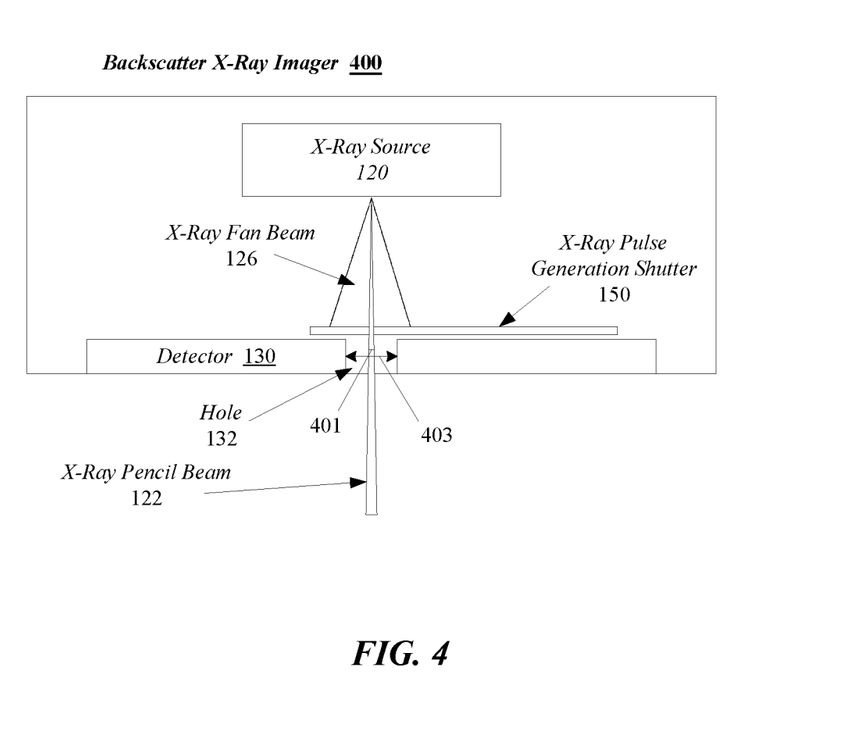
FIG. 4 illustrates an example backscatter x-ray imager according to some embodiments.

FIG. 4 illustrates cut away view of an example backscatter x-ray imager 400. The backscatter x-ray imager 400 can be implemented in an x-ray imaging system, such as, for example, the system 100 of FIGS. 1-2, the system 300 of FIG. 3, or another x-ray imaging system. In particular, the backscatter x-ray imager 400 can be implemented to generate an x-ray beam to be projected at target tissue and can capture backscattered x-rays resultant from the incidence of the x-ray beam on the target tissue. X-ray images, such as, for example, a mammographic image can be generated from indication so the backscattered x-rays.

Backscatter x-ray imager 400 includes an x-ray source 120 and a detector 130. In general, x-ray source 120 can be any x-ray source arranged to emit an x-ray beam 122. For example, the x-ray source 120 can be a system including an x-ray tube arranged to emit x-rays resulting from collisions of electrons within a vacuum. With some examples, the x-ray source can be arranged to emit a pencil beam 122. In some examples, the x-ray source can be arranged to emit an x-ray fan beam 126. The x-ray fan beam 126 can be formed into the x-ray pencil beam 122 via an x-ray pulse generation shutter as described below. In some examples, the x-ray source can be arranged to emit a low power (relative to conventional x-ray imaging sources) x-ray beam. For example, the x-ray beam 122 may have an energy quantified in the range of 15 to 65 kilo electron volts (kV). As a specific example, x-ray source 122 can emit x-ray beam 122 having an energy of around, or substantially, 40 kV.

Detector 130 includes a hole 132 through which x-ray beam 122 can be transmitted towards target tissue (see FIGS. 1-3). With some examples, the hole 132 can have a diameter larger than the diameter of the x-ray beam 122. For example, x-ray beam 122 may have a diameter 401 of between 0.01 millimeters (mm) to 4 mm while hole 132 can have a diameter 403 of between 1 mm and 6 mm. As a specific example, x-ray beam 122 may have a diameter 401 of 1 mm while hole 132 has a diameter 403 of 3 mm.

As noted, with some examples, backscatter x-ray imager 400 includes an x-ray pulse generation shutter 150. In general, the x-ray pulse generation shutter 150 is arranged to form pulses of x-ray beam 122. Additionally, with some examples, the x-ray pulse generation shutter 150 is arranged to form a pencil beam (e.g., beam 122) from a fan beam (beam 126). In some implementations, the x-ray pulse generation shutter 150 can include an aperture (not shown) through which a portion of x-ray fan beam 126 is transmitted, such that x-ray pencil beam 122 is emitted from backscatter x-ray imager 400. In some examples, x-ray pulse generation shutter 150 can be an opaque circular disc with multiple apertures spaced along the perimeter of the disk. During operation, the disk can be spun such that pulses of x-ray pencil beam 122 are emitted from the backscatter x-ray imager 400.

Figure 5:
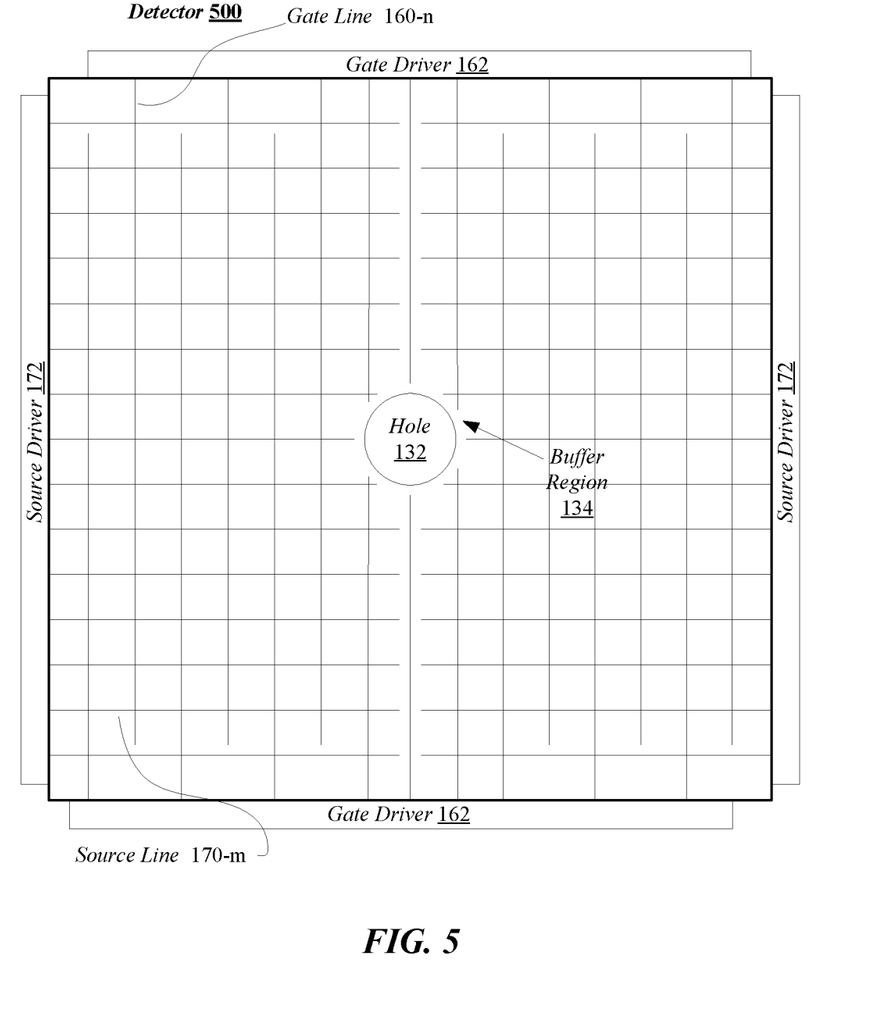
FIG. 5 illustrates a first example backscatter x-ray imager detector according to some embodiments.
Figure 6:
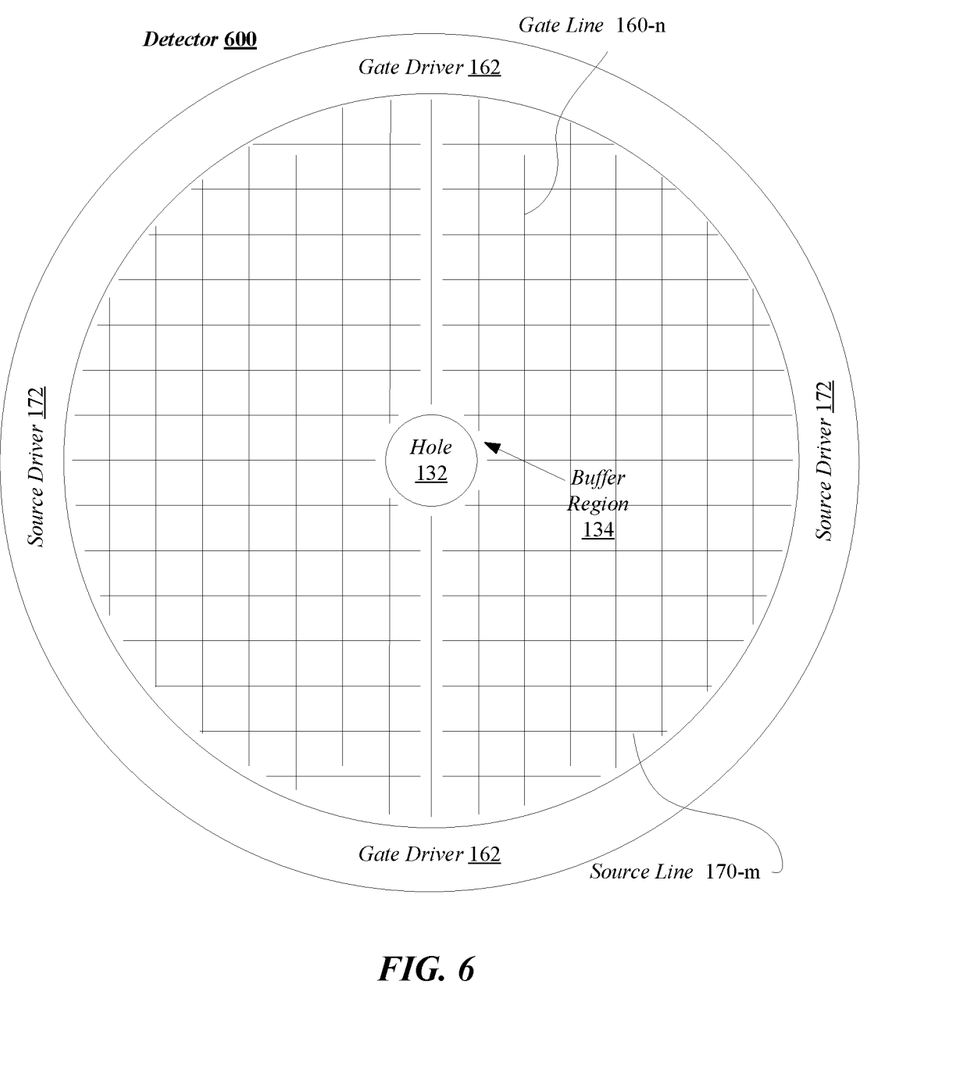
FIG. 6 illustrates a second example backscatter x-ray imager detector according to some embodiments.

FIGS. 5-6 illustrate first and second examples 500 and 600 of a detector, respectively. Either of the detectors 500 and 600 could be implemented as detector 130 of backscatter x-ray imager 120 discussed herein. It is noted that with some implementations, the detector 600 may provide an advantage. For example, the circular shape of the detector 600 may be more efficient in collecting backscattered x-rays 124 due to the circular nature of the x-ray beam 122. Furthermore, detector 600 may be realized in a smaller size while maintain the same ability to collect backscattered x-rays.

Detector 500 and 600 each include gate lines 160-$n$ and source lines 170-$m$, where n and m are positive integers. Furthermore, each of detectors 500 and 600 include a number of gate drivers 162 and source drivers 172 operably coupled to respective gate lines 160-$n$ and source lines 170-$m$. In general, the gate lines and source lines include sensing elements, which form a number of pixels on the surface of detector. When coupled to the drivers, x-rays can be detected at each pixel and a quantity or value of the amount of x-rays detected at each pixel determined. A variety of techniques are available for implementing the pixels, gate lines, source lines and connection bond pads to gate and source drivers such as thin film transistor process for flat panel displays.

Turning to FIG. 5, detector 500 includes hole 132, located substantially at the center of detector 500. As detailed above, the hole 132 provides an aperture with which x-ray beam 122 can be transmitted through detector 500. It is noted, that the hole 132 is depicted as circular in shape. However, this is not intended to be limiting and the hole 132 can have any shape suitable to communicate x-ray beam 122 through detector 500.

As can be seen, gate lines 160-$n$ and source lines 170-$m$ form a matrix across the surface of detector 500. However, of note, none of the gate lines 160-$n$ or source lines 170-$m$ cross over hole 132. Furthermore, gate lines 160-$n$ and source lines 170-$m$ are planned and positioned a distance away from hole 132, is essence, forming a buffer region 134 around hole 132. With some examples, semiconductor components (e.g., pixels, lines, bond pad for drivers, etc.) of detector 500 can be manufactured first, for example, using various flat panel display process and/or semiconductor manufacturing process. After which, hole 132 may be formed, such as, for example by cutting hole 132 with a laser. With some examples, during manufacturing, buffer region 134 may be covered and/or protected from etching, coating, polishing, and/or other processes steps involved in manufacturing detector 500.

In some examples, buffer region 134 and the center hole region 132 may be processed together with the pixels and gate and source lines on a substrate (e.g., a glass substrate, or the like). For example, detector 500 can be manufactured such that no active pixels, gate and source lines are built in the buffer region 134 and particularly in the area of hole 132 to prevent gate lines 160-$n$ and source lines 170-$m$ from damage during cutting of hole 132. More specifically, no active pixels, gate and source lines are built in buffer region 134 such that while cutting hole 132 (e.g., via a laser cutting process) and during operation where x-ray beam 122 is transmitted through hole 132 gate lines 160-$n$ and source lines 170-$m$ can be protected from damage.

In some embodiments, buffer region 134 may be coated with a metal shielding layer, for example, to protect the detector 500, and particularly to protect gate lines 160-$n$ and source lines 170-$m$ during cutting of hole 132 and during operation when x-ray beam 122 is transmitted through hole 132. With some examples, detector 500 further includes a glass cover (not shown) which may be cut with a hole to match or corresponding with hole 132 such that x-ray beam 122 passes through both the detector panel and the glass cover. This glass cover and semiconductor detector panel may be bonded together, using, for example, epoxy.

It is important to note, the difference in length between gate lines 160-$n$ and source lines 170-$m$ that intersect or are "interrupted" by the hole 132 and the gate lines 160-$n$ and source lines 170-$m$ that are not interrupted. Since there are uniformly distributed sensor pixels in the detector 500 with pitch width A across detector 500, x-ray signals reflected from human breast tissue may be detected by these sensor pixels. In general, detector 500 can operate as either a direct conversion detector or an indirect conversion detector. As a direct conversion detector, incident x-rays are directly converted into an electric charge at the sensor pixels while as an indirect conversion detector, incident x-rays are converted into light and then the light is converted into an electric charge at the sensor pixels.

During operation, source drivers 172 are electrically connected to sensor pixels via source lines 170-$m$ and arranged to read the electric charges from the sensor pixels via the source lines 170-$m$ while gate drivers 162 are electrically connected to the sensor pixels via the gate lines 160-$n$ and arranged to select the pixels one line a time. In order to read all the pixels, the source drivers 172 and gate drivers 162 can be connected to respective gate lines 170-$m$ and source lines 160-$n$ from both sides of the detector 500. This is not intended to be limiting, however, as implementations where source lines are driven from alternating sides of the detector can be provided. It is noted, in buffer region 134 where hole 132 is located, there are no pixels. As such, the length of the gate lines 160-$n$ and source lines 170-$m$ are reduced in this area. This is depicted in FIG. 5.

It is to be appreciated that the panel including detector 500 can be formed from conventional lithography techniques. As such, a photo mask would be needed for portions of the lithography process. To design and manufacture the photo mask, the length of each gate lines 160-$n$ and source line 170-$m$ needs to be defined accurately with respect to the size of the detector 500, the hole 132, and the buffer region 134. It is noted, that the size of the buffer region 134 can affect the x-ray signals received at the detector 500. For example, if the buffer region 134 is very wide, x-ray signals may be lost due to passing through the buffer region 134. It is further noted that reflective x-ray signals are stronger closer to their original x-ray beam. As such, the buffer region 134 is most proximate to the strongest reflective x-rays. Conversely, if the buffer region 134 is not large enough, metal features or residual metal from damage to sensor pixels (e.g., gate lines 160-$n$ and source lines 170-$m$) may generate shorts on the surface of detector 500, rendering the detector 500 unusable. As such, precise control over the size of buffer region 134, and therefore the length of gate lines 160-$n$ and source lines 170-$m$ is important.

An example of determining the length of the lines and thus number of the pixels for each line is given below. For this example, the layout of gate lines 160-$n$ and source lines 170-$m$ along with hole 132 and buffer region 134 of detector 500 as depicted in FIG. 5 are used. Specifically, it is assumed that the hole 132 is located in the center of detector 500 and is circular in shape. The length of the gate lines 160-$n$ can be defined by Equation 1 given below while the length of the source lines 170-$m$ can be defined by Equation 2 given below.

$$L_{GateLine}(N) = \frac{BA}{2} - \sqrt{\left(\frac{D}{2}\right)^2 - (AN)^2} \quad \text{Equation 1}$$

$$L_{SourceLine}(N) = \frac{CA}{2} - \sqrt{\left(\frac{D}{2}\right)^2 - (AN)^2} \quad \text{Equation 2}$$

In Equations 1 and 2, A is the size of each pixel in the detector 500, B is the number of gate lines 160-$n$, C the number of source lines 170-$m$, D is the diameter of hole 132 (or buffer region 134), and N is the line number away from the center of the panel, which is bound by 0 and $$\frac{D}{2A}.$$

An example panel having 1792 gate lines, 2048 source lines, a pixel resolution of 0.07 mm may be provided. This example panel may have a hole and buffer region diameter of 3 mm. Using the equations provided above, the corresponding lengths of each gate line 160-$n$ and source line 170-$m$ are determined. Thus, a corresponding photo mask for the layout can be generated and manufactured. It is noted, in the finished panel, no pixels will be formed or built in the area in which hole 132 will be cut. That is, buffer region 134 in which hole 132 will eventually be cut (e.g., after manufacturing of gate lines 160-*n* and source lines 170-*m*) is devoid of any sensor pixel features.

Turning to FIG. 6, detector 600 also includes hole 132, located substantially at the center of detector 600. Furthermore, detector 600 includes gate lines 160-*n* and source lines 170-*m* with a similar layout to the lines depicted in FIG. 5. However, as depicted, detector 600 is circular in shape as opposed to the rectangular or square shape of detector 500 depicted in FIG. 5. Gate drivers 162 and source drivers 172 can be laid out along the perimeter of the detector 600 as depicted. Determination of the lengths of gate lines 160-*n* and source lines 170-*m* for detector 600 are based on the equations 3 and 4 below.

$$L_{Gate\_or\_Source\_Line}(N) = \sqrt{\left(\frac{FA}{2}\right)^2 - (AN)^2} - \sqrt{\left(\frac{D}{2}\right)^2 - (AN)^2} \quad \text{Equation 3}$$

$$L_{Gate\_or\_Source\_Line}(N) = \sqrt{\left(\frac{FA}{2}\right)^2 - (AN)^2} \quad \text{Equation 4}$$

In Equation 3, A is the size of each pixel in the detector 600, F is the number of gate lines 160-*n* and source lines 170-*m*. Since the detector 600 is circular, the number of the source lines 170-*m* and gate lines 160-*n* are the same. D is the diameter of hole 132 (or buffer region 134). N is the line number away from the center of the panel 600, which is bound by 0 and $$\frac{D}{2A}.$$

The length of the gate lines 160-*n* and source lines 170-*m* outside the buffer region 134 will be defined by Equation 4.

An example panel having 1024 gate lines and source lines, a pixel resolution of 0.07 mm may be provided. This example panel may have a buffer region diameter of 3 mm. Using the equations provided above, the corresponding lengths of each gate line 160-*n* and source line 170-*m* are determined and the layout for a photomask used to form the gate lines 160-*n* and source lines 170-*m* having the determined lengths can be generated. It is noted, in the finished the panel 600, no pixels will be formed or built in the area in which hole 132 will be cut. That is, buffer region 134 in which hole 132 will eventually be cut (e.g., after manufacturing of gate lines 160-*n* and source lines 170-*m*) is devoid of any sensor pixel features.

Figure 7:
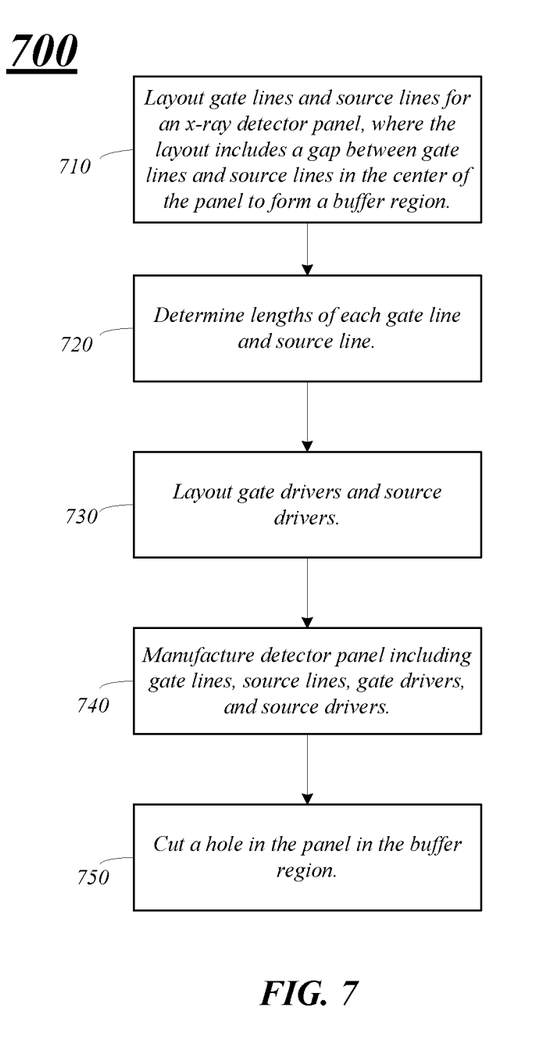
FIG. 7 illustrates a method to manufacture a backscatter x-ray detector panel according to some embodiments.
Figure 8:
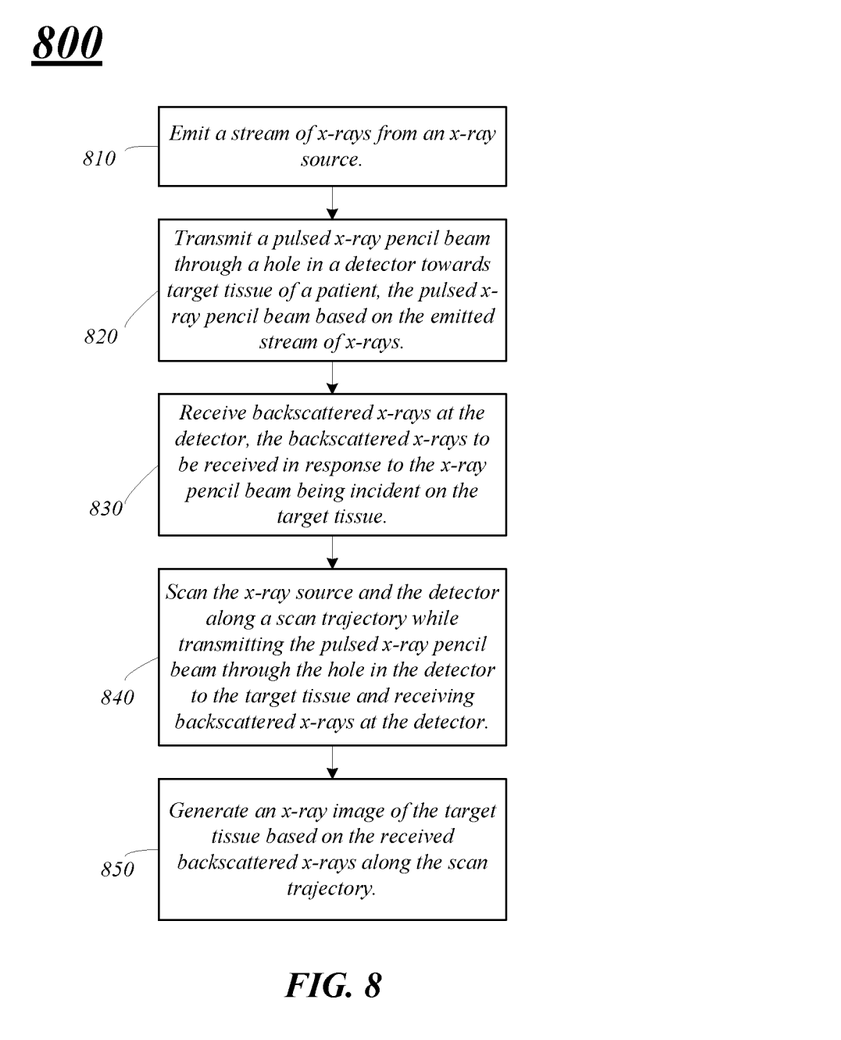
FIG. 8 illustrates a method to generate an x-ray image according to some embodiments.

FIGS. 7-8 illustrate methods 700 and 800. Method 700 depicts a technique to manufacture a detector according to examples given here while method 800 depicts a technique to generate an x-ray image using a backscatter x-ray imager according to examples given herein.

Turning to FIG. 7, the method 700 is depicted. Method 700 can begin at block 710. At block 710 "layout gate lines and source lines for an x-ray detector panel, where the layout includes a gap between gate lines and source lines in the center of the panel to form a buffer region" gate lines and source lines for a backscatter x-ray detector panel can be laid out, where the layout includes a region without gate lines or source lines. This region can be centered in the detector panel. For example, gate lines 162-*n* and source lines 170-*m* can be laid out for a detector panel (e.g., detector 500, detector 600, or the like) where the layout provides a gap between gate lines 160-*n* and source lines 170-*m* within the center of the panel to form buffer region 134 where hole 132 will eventually be cut.

Continuing to block 720 "determine lengths of each of the gate lines and source lines" lengths of the gate and source lines can be determined. For example, where the detector panel is square (e.g., detector 500) and the hole 132 and buffer region 134 is circular, lengths of the gate lines 160-*n* can be determined using Equation 1 while lengths of the source lines 170-*m* can be determined using Equation 2. As another example, where the detector panel is circular (e.g., detector 600) and the hole 132 and buffer region 134 are also circular, lengths of the gate lines 160-*n* can be determined using Equation 3 while lengths of the source lines 170-*m* can be determined using Equation 4

Continuing to block 730 "layout gate and source driver" the gate driver 162 and source driver 172 can be laid out. With some embodiments, bond pads for the gate drivers and source drivers can be laid out. For example, the gate driver bond pads and source driver bond pads can be laid out based in part on the lengths of the gate lines and source lines. Continuing to block 740 "manufacture detector panel including gate lines, source lines, gate driver, source driver" the detector panel can be manufactured per the layout from blocks 710 to 730. For example, a panel can be manufactured using conventional thin film transistors process or semiconductor processes based on the layout detailed herein. In some examples, the layout can include for the detector pixels, gate lines, source lines, ground lines and corresponding driver bond pads.

Continuing to block 750 "cut a hole in the panel in the buffer region" a hole can be cut in the detector panel within the center of the detector, such as, for example, within buffer region 134. In some embodiments, hole 132 can be cut in the center of the detector panel (e.g., detector 500, detector 600, or the like), using, for example, laser inscribing and/or laser cutting techniques.

Turning to FIG. 8, the method 800 is depicted. Method 800 can begin at block 810. At block 810 "Emit a stream of x-rays from an x-ray source" a stream of x-rays can be emitted from a source. For example, x-ray fan beam 126 can be emitted from x-ray source 120. Continuing to block 820 "transmit a pulsed x-ray pencil beam through a hole in a detector towards target tissue of a patient, the pulsed x-ray pencil beam based on the emitted stream of x-rays" an x-ray pencil beam can be transmitted through a detector towards target tissue. For example, x-ray pencil beam 122 can be formed from x-ray fan beam 126 and x-ray pulse generation shutter 150 and transmitted through hole 132 in detector 130 towards target tissue 191.

Continuing to block 830 "receive backscattered x-rays at the detector, the backscattered x-rays to be received in response to the x-ray pencil beam being incident on the target tissue" backscattered x-ray responsive to x-ray pencil beam incident on target tissue can be received at the detector. For example, backscattered x-rays 124, responsive to x-ray beam 122 incident at target tissue 191, can be received at detector 130.

Continuing to block 840 "scan the x-ray source and detector along a scan trajectory while transmitting the pulsed x-ray pencil beam through the hole in the detector to the target tissue and receiving backscattered x-rays at the detector" the target tissue can be exposed to the x-ray beam 122 while the x-ray source 120 and detector 130 are moved along scan trajectory 201. Backscattered x-rays 124 can be received by detector 130, responsive to exposure of target tissue 191 to x-ray beam 122, while the x-ray source 120 and detector 130 are moved along the scan trajectory 201.

Continuing to block 850 "generate an x-ray image of the target tissue based on the backscattered x-rays received along the scan trajectory" an x-ray image of the target tissue can be generated from the received backscattered x-rays. For example, backscattered x-rays 124 can be used to generate an x-ray image of target tissue 191.

Figure 9:
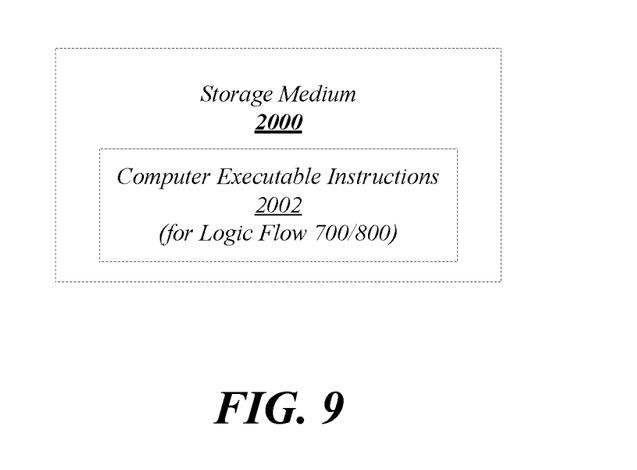
FIG. 9 illustrates a computer readable storage medium according to some embodiments.

FIG. 9 illustrates an embodiment of a storage medium 2000. The storage medium 2000 may comprise an article of manufacture. In some examples, the storage medium 2000 may include any non-transitory computer readable medium or machine readable medium, such as an optical, magnetic or semiconductor storage. The storage medium 2000 may store various types of computer executable instructions e.g., 2002). For example, the storage medium 2000 may store various types of computer executable instructions to implement technique 700. For example, the storage medium 2000 may store various types of computer executable instructions to implement technique 800.

Examples of a computer readable or machine-readable storage medium may include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The examples are not limited in this context.

FIG. 10 illustrates one embodiment of a system 3000. In various embodiments, system 3000 may be representative of a system or architecture suitable for use with one or more embodiments described herein, such as device 100.

As shown in this figure, system 3000 may include multiple elements. One or more elements may be implemented using one or more circuits, components, registers, processors, software subroutines, modules, or any combination thereof, as desired for a given set of design or performance constraints. Although this figure shows a limited number of elements in a certain topology by way of example, it can be appreciated that more or less elements in any suitable topology may be used in system 3000 as desired for a given implementation. The embodiments are not limited in this context.

In various embodiments, system 3000 may include a computing device 3005 which may be any type of computer or processing device including a personal computer, desktop computer, tablet computer, netbook computer, notebook computer, laptop computer, server, server farm, blade server, or any other type of server, and so forth.

Examples of a computing device also may include computers that are arranged to be worn by a person, such as a wrist computer, finger computer, ring computer, eyeglass computer, belt-clip computer, arm-band computer, shoe computers, clothing computers, and other wearable computers. In embodiments, for example, a mobile computing device may be implemented as a smart phone capable of executing computer applications, as well as voice communications and/or data communications. Although some embodiments may be described with a mobile computing device implemented as a smart phone by way of example, it may be appreciated that other embodiments may be implemented using other wireless mobile computing devices as well. The embodiments are not limited in this context.

In various embodiments, computing device 3005 may include processor circuit 3002. Processor circuit 3002 may be implemented using any processor or logic device. The processing circuit 3002 may be one or more of any type of computational element, such as but not limited to, a microprocessor, a processor, central processing unit, digital signal processing unit, dual core processor, mobile device processor, desktop processor, single core processor, a system-on-chip (SoC) device, complex instruction set computing (CISC) microprocessor, a reduced instruction set (RISC) microprocessor, a very long instruction word (VLIW) microprocessor, or any other type of processor or processing circuit on a single chip or integrated circuit. The processing circuit 3002 may be connected to and communicate with the other elements of the computing system via an interconnect 743, such as one or more buses, control lines, and data lines.

In one embodiment, computing device 3005 may include a memory unit 3004 to couple to processor circuit 3002. Memory unit 3004 may be coupled to processor circuit 3002 via communications bus 3053, or by a dedicated communications bus between processor circuit 3002 and memory unit 3004, as desired for a given implementation. Memory unit 04 may be implemented using any machine-readable or computer-readable media capable of storing data, including both volatile and non-volatile memory. In some embodiments, the machine-readable or computer-readable medium may include a non-transitory medium. The embodiments are not limited in this context.

Computing device 3005 may include a graphics processing unit (GPU) 3006, in various embodiments. The GPU 3006 may include any processing unit, logic or circuitry optimized to perform graphics-related operations as well as the video decoder engines and the frame correlation engines. The GPU 3006 may be used to render 2-dimensional (2-D) and/or 3-dimensional (3-D) images for various applications such as video games, graphics, computer-aided design (CAD), simulation and visualization tools, imaging, etc. Various embodiments are not limited in this manner; GPU 3006 may process any type of graphics data such as pictures, videos, programs, animation, 3D, 2D, objects images and so forth.

In some embodiments, computing device 3005 may include a display controller 3008. Display controller 3008 may be any type of processor, controller, circuit, logic, and so forth for processing graphics information and displaying the graphics information. The display controller 3008 may receive or retrieve graphics information from one or more buffers. After processing the information, the display controller 3008 may send the graphics information to a display.

In various embodiments, system 3000 may include a transceiver 3044. Transceiver 3044 may include one or more radios capable of transmitting and receiving signals using various suitable wireless communications techniques. Such techniques may involve communications across one or more wireless networks. Exemplary wireless networks include (but are not limited to) wireless local area networks (WLANs), wireless personal area networks (WPANs), wireless metropolitan area network (WMANs), cellular networks, and satellite networks. In communicating across such networks, transceiver 3044 may operate in accordance with one or more applicable standards in any version. The embodiments are not limited in this context.

In various embodiments, computing device 3005 may include a display 3045. Display 3045 may constitute any display device capable of displaying information received from processor circuit 3002, graphics processing unit 3006 and display controller 3008.

In various embodiments, computing device 3005 may include storage 3046. Storage 3046 may be implemented as a non-volatile storage device such as, but not limited to, a magnetic disk drive, optical disk drive, tape drive, an internal storage device, an attached storage device, flash memory, battery backed-up SDRAM (synchronous DRAM), and/or a network accessible storage device. In embodiments, storage 3046 may include technology to increase the storage performance enhanced protection for valuable digital media when multiple hard drives are included, for example. Further examples of storage 3046 may include a hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of DVD devices, a tape device, a cassette device, or the like. The embodiments are not limited in this context.

In various embodiments, computing device 3005 may include one or more I/O adapters 3047. Examples of I/O adapters 3047 may include Universal Serial Bus (USB) ports/adapters, IEEE 1394 Firewire ports/adapters, and so forth. The embodiments are not limited in this context.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. An apparatus for an x-ray system to generate x-ray images of a breast, the apparatus comprising:
   an x-ray source arranged to emit a stream of x-rays;
   a detector disposed proximate to the source, the detector comprising a hole through which the stream of x-rays is transmitted towards target tissue, the detector arranged to detect backscattered x-rays resulting from incidence of the stream of x-rays on the target tissue;
   a plurality of gate lines laid out in a first direction across a surface of the detector, wherein the plurality of gate lines are interrupted in a buffer region, the buffer region comprising a diameter equal to or greater than a diameter of the hole; and
   a plurality of source lines laid out in a second direction across the surface of the detector, wherein the plurality of source lines are interrupted in the buffer region, the first direction is substantially perpendicular to the second direction.

2. The apparatus of claim 1, comprising a motor coupled to both the x-ray source and the detector, the motor to move the x-ray source and the detector in tandem along a scan trajectory to expose an area of the target tissue to the stream of x-rays.

3. The apparatus of claim 1, comprising:
   a support member coupled to both the x-ray source and the detector; and
   an actuator coupled to the support member and arranged to move the support member to move the x-ray source and the detector in tandem along a scan trajectory to expose an area of the target tissue to the stream of x-rays.

4. The apparatus of claim 3, the support member comprising a first support member, the apparatus comprising:
   an articulated joint coupled to the first support member and the actuator; and
   a second support member coupled to the articulated joint, the articulated joint to allow the first support member to move in at least one axis of movement respective to the second support member, the actuator to move the first support member in the at least one axis of movement.

5. The apparatus of claim 1, wherein the stream of x-rays is a pencil beam.

6. The apparatus of claim 1, wherein the stream of x-rays is a fan beam, the x-ray source comprising an x-ray pulse generation shutter to emit pulses of an x-ray pencil beam from the fan beam.

7. The apparatus of claim 6, the x-ray pulse generation shutter comprising:
   an opaque disk including a plurality of apertures disposed along a perimeter of the disk, the opaque disk position between the x-ray source and the hole in the detector; and
   a shutter motor coupled to the opaque disk and arranged to spin the opaque disk to form x-ray pencil beam pulses to be transmitted through the hole in the detector.

8. The apparatus of claim 1, wherein the hole is positioned in substantially the center of the detector.

9. The apparatus of claim 8, wherein the buffer region is disposed in substantially the center of the detector.

10. The apparatus of claim 9, wherein the hole is positioned within the buffer region.

11. The apparatus of claim 1, wherein the detector comprises a detector panel having a substantially circular shape.

12. The apparatus of claim 1, wherein the detector comprises a detector panel having a rectangular or square shape.

13. A method to generate an x-ray image of target tissue of a patient, comprising:
   emitting a stream of x-rays from an x-ray source;
   transmitting a pulsed x-ray pencil beam through a hole in a detector to target tissue, the pulsed x-ray pencil beam based in part on the emitted stream of x-rays, wherein the detector comprises a plurality of gate lines laid out in a first direction across a surface of the detector, the plurality of gate lines interrupted in a buffer region, the buffer region comprising a diameter equal to or greater than a diameter of the hole, and a plurality of source lines laid out in a second direction across the surface of the detector, the plurality of source lines are interrupted in the buffer region, wherein the first direction is substantially perpendicular to the second direction;
   receiving backscattered x-rays at the detector, the backscattered x-rays responsive to incidence of the pulsed x-ray pencil beam on the target tissue;
   scanning the x-ray source and the detector along a scan trajectory to expose an area of the target tissue to the pulsed x-ray pencil beam and receiving, at the detector, backscattered x-rays responsive to exposure of the area of the target tissue to the pulsed x-ray pencil beam; and
   generating an x-ray image of the area of the target tissue based in part on the received backscattered x-rays.

14. The method of claim 13, comprising scanning the x-ray source and detector along the scan trajectory using a motor.

15. The method of claim 13, comprising scanning the x-ray source and detector along the scan trajectory using a robotic arm.

16. The method of claim 13, wherein the stream of x-rays is a pencil beam.

17. The method of claim 13, wherein the emitted stream of x-rays is a fan beam, the method comprising spinning an x-ray pulse generation shutter to emit the pulsed x-ray pencil beam based in part on the x-ray fan beam.

18. The method of claim 17, the x-ray pulse generation shutter comprising:
   an opaque disk including a plurality of apertures disposed along a perimeter of the disk, the opaque disk position between the x-ray source and the hole in the detector; and
   a shutter motor coupled to the opaque disk and arranged to spin the opaque disk to form x-ray pencil beam pulses to be transmitted through the hole in the detector.

19. The method of claim 13, wherein the hole is positioned in substantially the center of the detector, and wherein the buffer region is disposed in substantially the center of the detector.

20. The method of claim 19, wherein the hole is positioned within the buffer region.

21. The method of claim 13, wherein the detector comprises a detector panel having a substantially circular shape.

22. The method of claim 13, wherein the detector comprises a detector panel having a rectangular or square shape.

23. An apparatus to scan an x-ray beam across breast tissue and detect backscattered x-rays resulting from incidence of the x-ray beam on the breast tissue, comprising means to perform the method of claim 13.

24. At least one non-transitory computer readable medium, which comprises a plurality of instructions, which in response to being executed on a processor circuit of a x-ray device causes the processor circuit to implement the method of claim 13.

\* \* \* \* \*